(12) United States Patent
Mittelstein et al.

(10) Patent No.: US 11,229,809 B2
(45) Date of Patent: Jan. 25, 2022

(54) SELECTIVE DISRUPTION OF NEOPLASTIC CELLS VIA RESONANT HARMONIC EXCITATION

(71) Applicant: California Institute of Technology, Pasadena, CA (US)

(72) Inventors: David Reza Mittelstein, Pasadena, CA (US); Morteza Gharib, Pasadena, CA (US); Stefanie Heyden, Pasadena, CA (US); Michael Ortiz, Pasadena, CA (US); Mikhail G. Shapiro, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 919 days.

(21) Appl. No.: 15/912,359

(22) Filed: Mar. 5, 2018

(65) Prior Publication Data

US 2018/0256922 A1    Sep. 13, 2018

Related U.S. Application Data

(60) Provisional application No. 62/466,591, filed on Mar. 3, 2017.

(51) Int. Cl.
*A61N 7/00* (2006.01)
*A61M 37/00* (2006.01)
(Continued)

(52) U.S. Cl.
CPC ............... *A61N 7/00* (2013.01); *A61B 8/485* (2013.01); *A61M 37/0092* (2013.01);
(Continued)

(58) Field of Classification Search
CPC ..... A61B 8/4416; A61B 8/485; A61B 8/5246; A61B 8/5261; A61B 8/58;
(Continued)

(56) References Cited

U.S. PATENT DOCUMENTS

| 8,591,419 B2 * | 11/2013 | Tyler ............... A61N 5/0622 600/439 |
| 2005/0214268 A1 * | 9/2005 | Cavanagh, III ........ A61B 18/02 424/93.21 |

(Continued)

OTHER PUBLICATIONS

Aubry et al., "The road to clinical use of high-intensity focused ultrasound for liver cancer: technical and clinical consensus", Journal of Therapeutic Ultrasound, Aug. 1, 2013, vol. 1, No. 13, 7 pages, https://doi.org/10.1186/2050-5736-1-13.

(Continued)

*Primary Examiner* — Shefali D Patel
(74) *Attorney, Agent, or Firm* — KPPB LLP

(57) ABSTRACT

Systems and methods for targeting specific cell types by selective application of ultrasonic harmonic excitation at a resonance frequency ("oncotripsy") for the specific cell types are presented. The systems and the methods result in permeabilization, lysis, and/or death of the targeted specific cell types by using ultrasonic harmonic excitations that have a frequency and a pulse duration specifically tuned to disrupt nuclear membranes of the targeted specific cell types by inducing a destructive vibrational response therein while leaving non-targeted cell types intact. Target cells may be neoplastic.

12 Claims, 11 Drawing Sheets

(51) Int. Cl.
| | |
|---|---|
| *A61B 8/08* | (2006.01) |
| *A61B 17/3205* | (2006.01) |
| *A61B 5/055* | (2006.01) |
| *A61B 18/00* | (2006.01) |
| *A61B 90/00* | (2016.01) |
| *A61B 17/00* | (2006.01) |

(52) U.S. Cl.
CPC .............. *A61B 5/055* (2013.01); *A61B 8/5261* (2013.01); *A61B 17/3205* (2013.01); *A61B 2017/00154* (2013.01); *A61B 2018/0066* (2013.01); *A61B 2018/00642* (2013.01); *A61B 2018/00732* (2013.01); *A61B 2090/374* (2016.02); *A61B 2090/378* (2016.02); *A61M 2205/058* (2013.01)

(58) Field of Classification Search
CPC ........ A61B 2090/378; A61M 37/0092; A61M 2205/058; A61M 2205/3375; A61M 2230/005; A61N 7/00; A61N 2007/0004; A61N 2007/0073
See application file for complete search history.

(56) References Cited

U.S. PATENT DOCUMENTS

| | | | |
|---|---|---|---|
| 2006/0034943 A1 | 2/2006 | Tuszynski | |
| 2006/0058592 A1 | 3/2006 | Bouma et al. | |
| 2008/0082110 A1* | 4/2008 | Rodriguez Ponce | A61B 34/30 606/130 |
| 2009/0198231 A1 | 8/2009 | Esser et al. | |
| 2010/0113983 A1* | 5/2010 | Heckerman | A61N 7/00 601/2 |
| 2011/0098987 A1 | 4/2011 | Isoshima et al. | |
| 2012/0059865 A1 | 3/2012 | Shao et al. | |
| 2013/0131557 A1* | 5/2013 | Kline | A61N 7/00 601/2 |
| 2017/0165506 A1 | 6/2017 | Ortiz et al. | |
| 2017/0266438 A1 | 9/2017 | Sano et al. | |

OTHER PUBLICATIONS

Bruix et al., "Evidence-Based Diagnosis, Staging, and Treatment of Patients with Hepatocellular Carcinoma", Gastroenterology, Apr. 2016, vol. 150, No. 4, pp. 835-853, https://doi.org/10.1053/j.gastro.2015.12.041.

Caille, N. et al., "Contribution of the nucleus to the mechanical properties of endothelial cells", J. Biomech., vol. 35, 2002, pp. 177-187.

Cartagena, A. et al., "Local Viscoelastic Properties of Live Cells Investigated Using Dynamic and Quasi-Static Atomic Force Microscopy Methods", Biophysical Journal, vol. 106, Mar. 2014, pp. 1033-1043.

Chakraborty et al., "The difficulties in cancer treatment", Ecancermedicalscience, Published Online: Nov. 14, 2012, vol. 6, pp. ed16, 5 pgs, doi: 10.3332/ecancer.2012.ed16.

Clegg, J. S., "Properties and metabolism of the aqueous cytoplasm and its boundaries", Am. J. Physiol. 246, 1984, pp. R133-R151.

Cohen-Inbar et al., "Focused ultrasound-aided immunomodulation in glioblastoma multiforme: a therapeutic concept", Journal of Therapeutic Ultrasound, Jan. 22, 2016, vol. 4, No. 2, 9 pages, https://doi.org/10.1186/S40349-016-0046-y.

Couture et al., "Review of ultrasound mediated drug delivery for cancer treatment: updates from pre-clinical studies", Translational Cancer Research, vol. 3, No. 5, Oct. 2014, pp. 494-511.

Cross, S. E. et al., "Nanomechanical analysis of cells from cancer patients", Nature Nanotechnology, Dec. 2, 2007, vol. 2, pp. 780-783.

Dahl, K. N. et al., "The nuclear envelope lamina network has elasticity and a compressibility limit suggestive of a molecular shock absorber", Journal of Cell Science, Jun. 14, 2004, vol. 117, pp. 4779-4786.

Della Rocca, "The science of ultrasound therapy for fracture healing", Indian Journal of Orthopaedics, 2009, vol. 43, No. 2, pp. 121-126, doi: 10.4103/0019-5413.50845.

Eisenmenger, "The mechanisms of stone fragmentation in ESWL", Ultrasound in Medicine & Biology, vol. 27, Issue 5, May 2001, pp. 683-693, https://doi.org/10.1016/S0301-5629(01)00345-3.

Evans, E. A. et al., "Elastic Area Compressibility Modulus of Red Cell Membrane", Biophysical Journal, 1976, vol. 16, pp. 585-595.

Evans, E. A. et al., "Membrane Viscoelasticity", Biophys J., vol. 16, No. 1, 1976, pp. 1-11.

Fan et al., "Spatiotemporally controlled single cell sonoporation", PNAS, Oct. 9, 2012, vol. 109, No. 41, p. 16486-16491, https://doi.org/10.1073/pnas.1208198109.

Fass, "Imaging and cancer: A review", Molecular Oncology, vol. 2, Issue 2, Aug. 2008, pp. 115-152, https://doi.org/10.1016/j.molonc.2008.04.001.

Feril Jr. et al., "Therapeutic potential of low-intensity ultrasound (part 1) thermal and sonomechanical effects", Journal of Medical Ultrasonics, Dec. 2008, vol. 35, Issue 4, pp. 153-160.

Fraldi et al., "A Frequency-Based Hypothesis for Mechanically Targeting and Selectively Attacking Cancer Cells", Journal of the Royal Society Interface, Oct. 6, 2015, vol. 12, No. 111: 20150656, pp. 1-16.

Fuhrmann, A. et al., "AFM stiffness nanotomography of normal, metaplastic and dysplastic human esophageal cells", Physical Biology, Feb. 7, 2011, vol. 8, pp. 1-10.

Furusawa et al., "Effects of therapeutic ultrasound on the nucleus and genomic DNA", Ultrasonics Sonochemistry, vol. 21, Issue 6, Nov. 2014, pp. 2061-2068, https://doi.org/10.1016/j.ultsonch.2014.02.028.

Guilak, F., "Viscoelastic Properties of the Cell Nucleus", Biochemical and Biophysical Research Communications, Dec. 21, 1999, vol. 269, pp. 781-786.

Guttman et al., "Nuclear-Nucleolar Volume Ratio in Cancer", American Journal of Cancer, 1935, pp. 802-806.

Handwerger, K. E. et al., "Cajal Bodies, Nucleoli, and Speckles in the Xenopus Oocyte Nucleus Have a Low-Density, Sponge-like Structure", Molecular Biology of the Cell, Jan. 2005, vol. 16 (1), pp. 202-211.

Hersh et al., "Emerging Applications of Therapeutic Ultrasound in Neuro-oncology: Moving Beyond Tumor Ablation", Neurosurgery, vol. 79, Issue 5, Nov. 1, 2016, pp. 643-654, https://doi.org/10.1227/NEU.0000000000001399.

Heyden et al., "Investigation of the influence of viscoelasticity on oncotripsy", Computer Methods in Applied Mechanics and Engineering, Feb. 1, 2017, vol. 314, pp. 314-322, https://doi.org/10.1016/j.cma.2016.08.026.

Heyden et al., "Oncotripsy: Targeting cancer cells selectively via resonant harmonic excitation", arXiv:1512.03320v1 [physics.bio-ph], Dec. 7, 2015, 22 pgs.

Houchmandzadeh et al., "Elasticity and Structure of Eukaryote Chromosomes Studied by Micromanipulation and Micropipette Aspiration", The Journal of Cell Biology, Oct. 6, 1997, vol. 139, No. 1, pp. 1-12.

Hsiao et al., "Clinical Application of High-intensity Focused Ultrasound in Cancer Therapy", Journal of Cancer, Jan. 3, 2016, vol. 7, No. 3, pp. 225-231, doi: 10.7150/jca.13906.

Ignatiadis et al., "Circulating Tumor Cells and Circulating Tumor DNA Challenges and Opportunities on the Path to Clinical Utility", Clinical Cancer Research, Nov. 2015, vol. 21, No. 21, pp. 4786-4800, DOI: 10.1158/1078-0432.CCR-14-1190.

Jay, A. W. L., "Viscoelastic Properties of the Human Red Blood Cell Membrane", Biophysical Journal, 1973, vol. 13, No. 11, pp. 1166-1182.

Kattan, "Matlab Guide to Finite Element", Springer-Verlag Berlin Heidelberg, Year. 2008, Chapter 11 and Chapter 15, 64 pgs.

Kim et al., "Characterization of cellular elastic modulus using structure based double layer model", Med. Biol. Engineering and Computing, Jan. 8, 2011, vol. 49, No. 4, pp. 453-462.

(56) References Cited

OTHER PUBLICATIONS

Kochmann et al., "Analytical stability conditions for elastic composite materials with a non-positive-definite phase", Proceedings of the Royal Society A, Feb. 15, 2012, pp. 1-25.
Kondziolka et al., "The biology of radiosurgery and its clinical applications for brain tumors", Neuro-Oncology, vol. 17, Issue 1, Jan. 1, 2015, pp. 29-44, https://doi.org/10.1093/neuonc/nou284.
Konno et al., "Non-invasive Stiffness Detection Method for Living Cell Nucleus by Using Piezoelectric Micro Sensor", IFMBE Proceedings, vol. 39, 2013, Springer,pp. 290-293.
Krasovitski et al., "Intramembrane cavitation as a unifying mechanism for ultrasound-induced bioeffects", PNAS, Feb. 7, 2011, 6 pages, https://doi.org/10.1073/pnas.1015771108.
Krodel, S et al., "3D Auxetic Microlattices with Independently Controllable Acoustic Band Gaps and Quasi-Static Elastic Moduli", Advanced Engineering Materials, 2014, vol. 16, No. 4, pp. 357-363.
Lammertink et al., "Sonochemotherapy: from bench to bedside", Frontiers in Pharmacology, Jul. 10, 2015, vol. 6, Article 138, pp. 1-17.
Lee et al., "Mechanical Properties of Normal Breast Cells and Metastatic Cancer Cells in Co-Culture", Biophysical Journal, Feb. 12, 2017, vol. 112, No. 3, p. 124a.
Lekka, "Discrimination Between Normal and Cancerous Cells Using AFM", BioNanoScience, Mar. 2016, vol. 6, Issue 1, pp. 65-80, DOI 10.1007/S12668-016-0191-3.
Lentacker, I. et al., "Understanding ultrasound induced sonoporation Definitions and underlying mechanisms", Advanced Drug Delivery Reviews, Nov. 21, 2013, vol. 72, pp. 49-64.
Levental, K. R. et al., "Matrix Crosslinking Forces Tumor Progression by Enhancing Integrin Signaling", Cell, Nov. 25, 2009, vol. 139, pp. 891-906.
Li et al., "Yield Strength of Human Erythrocyte Membranes to Impulsive Stretching", Biophysical Journal, Aug. 2013, vol. 105, pp. 872-879.
Lieleg et al., "Cytoskeletal Polymer Networks: Viscoelastic Properties are Determined by the Microscopic Interaction Potential of Cross-links", Biophysical Journal, Jun. 2009, vol. 96, pp. 4725-4732.
Liu et al., "Bloch Wave Approach for the Analysis of Sequential Bifurcations in Bilayer Structures", Proc. R. Soc. A 471: 20150493, Nov. 6, 2015, pp. 1-16.
Lodish, H et al., "Molecular Cell Biology", Molecular Cell Biology, 5th Edition, 2004, WH Freeman, New York. Presented in 5 parts. 979 pages.
Louw et al., "Mechanotransduction of Ultrasound is Frequency Dependent Below the Cavitation Threshold", Ultrasound in Medicine & Biology, vol. 39, Issue 7, Jul. 2013, pp. 1303-1319, https://doi.org/10.1016/j.ultrasmedbio.2013.01.015.
Malietzis et al., "High-intensity focused ultrasound: advances in technology and experimental trials support enhanced utility of focused ultrasound surgery in oncology", The British Journal of Radiology, vol. 86, Issue 1024, 2013, 12 pages, https://doi.org/10.1259/bjr.20130044.
McGahan et al., "Hepatic Ablation with Use of Radio-Frequency Electrocautery in the Animal Model", Journal of Vascular and Interventional Radiology, May 1992, vol. 3, Issue 2, pp. 291-297, DOI: https://doi.org/10.1016/S1051-0443(92)72028-4.
Milner et al., "Finite-Element Modeling of Viscoelastic Cells During High-Frequency Cyclic Strain", Journal of Functional Biomaterials, 2012, No. 3, pp. 209-224.
Moran, U. et al., "Snapshot: Key Numbers in Biology", Cell, vol. 141, Jun. 25, 2010, pp. 1262-1262e1.
Niranjan et al., "Role of adjuvant or salvage radiosurgery in the management of unresected residual or progressive glioblastoma multiforme in the pre-bevacizumab era", Journal of Neurosurgery, Apr. 2015, vol. 122, No. 4, pp. 757-765.
Paszek, M. J. et al., "Tensional homeostasis and the malignant phenotype", Cancer Cell, Sep. 2005, vol. 8, pp. 241-254.

Pogoda et al., "Compression stiffening of brain and its effect on mechanosensing by glioma cells", New Journal of Physics, vol. 16, Jul. 2014, Article 075002, 15 pages.
Ricard et al., "Ventilator-Induced Lung Injury", Organ System Function and Failure, Part II, 1st Edition, 2006, CRC Press, Boca Raton, FL, Chapter 45, pp. 719-730.
Rooze et al., "Dissolved gas and ultrasonic cavitation—A review", Ultrasonics Sonochemistry, vol. 20, Issue 1, Jan. 2013, pp. 1-11, https://doi.org/10.1016/j.ultsonch.2012.04.013.
Samandari et al., "Ultrasound induced strain cytoskeleton rearrangement An experimental and simulation study", Journal of Biomechanics, vol. 60, Jul. 26, 2017, pp. 39-47, https://doi.org/10.1016/j.jbiomech.2017.06.003.
Schrader et al., "Matrix Stiffness Modulates Proliferation, Chemotherapeutic Response, and Dormancy in Hepatocellular Carcinoma Cells", Hepatology, vol. 53, No. 4, 2011, pp. 1192-1205.
Shen et al., "The effects of low-frequency ultrasound and microbubbles on Yabbit hepatic tumors", Experimental Biology and Medicine, First Published Apr. 9, 2014, vol. 239, No. 6, pp. 747-757, https://doi.org/10.1177/1535370214525320.
Silvestrini et al., "Priming is key to effective incorporation of image-guided thermal ablation into immunotherapy protocols", JCI Insight, Mar. 23, 2017. vol. 2, No. 6, Article e90521, 16 pages, doi: 10.1172/jci.insight.90521.
Swaminathan et al., "Mechanical Stiffness Grades Metastatic Potential in Patient Tumor Cells and in Cancer Cell Lines", Cancer Research, vol. 71, No. 15, Jun. 3, 2011, pp. 5075-5080.
Teicher, "Perspective: Opportunities in recalcitrant, rare and neglected tumors", Oncology Reports, Sep. 2013, vol. 30, Issue 3, pp. 1030-1034, Published online on Jul. 2, 2013, https://doi.org/10.3892/or.2013.2581.
Tempany et al., "Focused Ultrasound Surgery in Oncology: Overview and Principles", Radiology, Published Online: Apr. 1, 2011, vol. 259, No. 1, pp. 39-56, https://doi.org/10.1148/radiol.11100155.
Ter Haar et al., "Tissue Destruction with Focused Ultrasound in vivo", European Urology, 1993, vol. 23, Suppl. 1, pp. 8-11, https://doi.org/10.1159/000474672.
Unga et al., "Ultrasound induced cancer immunotherapy", Advanced Drug Delivery Reviews, vol. 72, Jun. 15, 2014, pp. 144-153, https://doi.org/10.1016/j.addr.2014.03.004.
Van Diest et al., "Prognostic value of proliferation in invasive breast cancer a review", Journal of Clinical Pathology, 2004, vol. 57, No. 7, pp. 675-681, http://dx.doi.org/10.1136/jcp.2003.010777.
Venkatesh et al., "MR Elastography of Liver Tumors: Preliminary Results", American Journal of Roentgenology, Jun. 2008, vol. 190, No. 6, pp. 1534-1540.
Wiklund, "Acoustofluidics 12: Biocompatibility and cell viability in microfluidic acoustic resonators", Lab Chip, 2012, vol. 12, No. 11, pp. 2018-2028.
Wood et al., "A Review of Low-Intensity Ultrasound for Cancer Therapy", Ultrasound in Medicine & Biology, Apr. 2015, vol. 41, No. 4, pp. 905-928, https://doi.org/10.1016/j.ultrasmedbio.2014.11.019.
Ye et al., "Frequency Dependence of Ultrasound Neurostimulation in the Mouse Brain", Ultrasound in Medicine & Biology, Jul. 2016, vol. 42, No. 7, pp. 1512-1530, https://doi.org/10.1016/j.ultrasmedbio.2016.02.012.
Zhang et al., "Effects of high-intensity focused ultrasound for treatment of abdominal lymph node metastasis from gastric cancer.", Journal of Ultrasound in Medicine, vol. 34, Issue 3, Mar. 2015, pp. 435-440, https://doi.org/10.7863/ultra.34.3.435.
Zhang et al., "Mechanical properties of hepatocellular carcinoma cells", World Journal of Gastroenterology, Apr. 15, 2002, vol. 8, No. 2, pp. 243-246.
Zhou, "High intensity focused ultrasound in clinical tumor ablation", World Journal of Clinical Oncology, Jan. 10, 2011, vol. 2, No. 1, pp. 8-27, doi: 10.5306/wjco.v2.i1.8.
Davidson et al., "Molecular Expressions: Cell biology and microscopy, Structure and Function of cells & viruses", The Cell Nucleus, Year: 2007 https://micro.magnet.fsu.edu/cells/nucleus/nucleus.html.

* cited by examiner

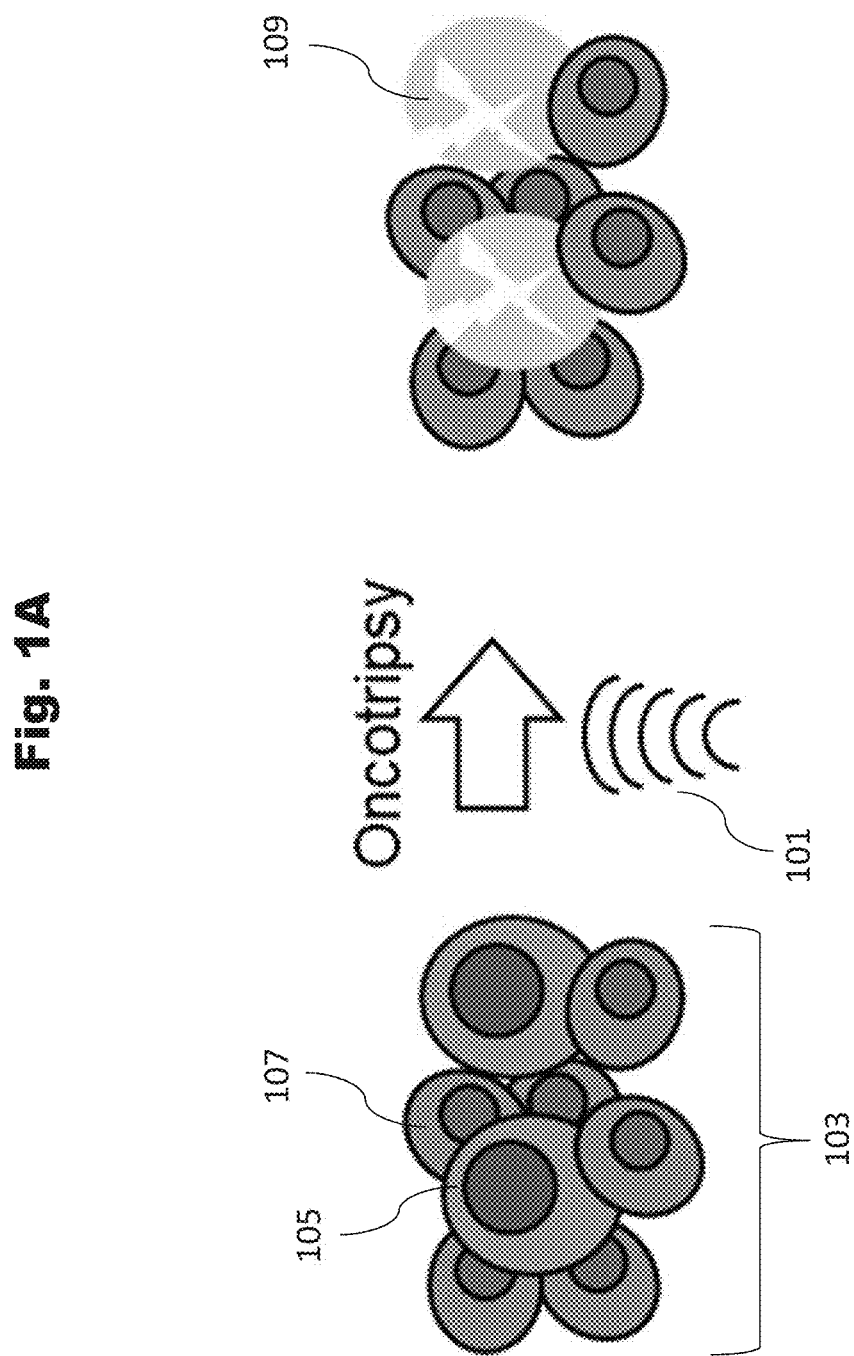

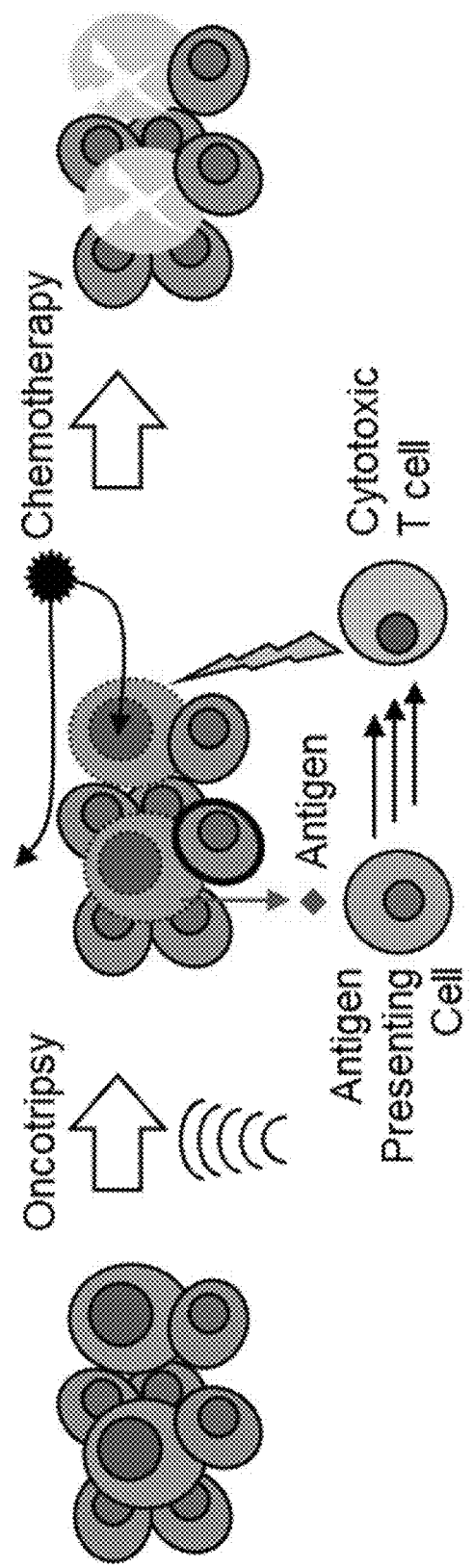

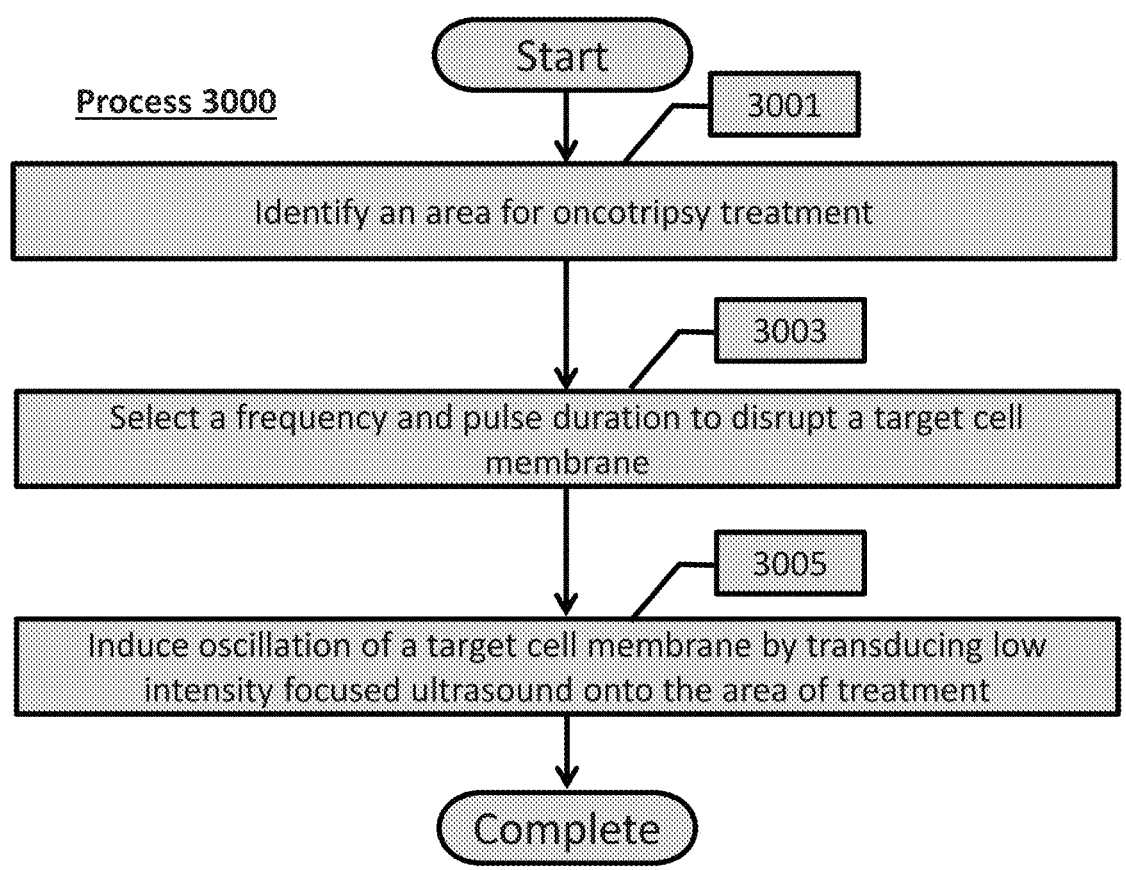

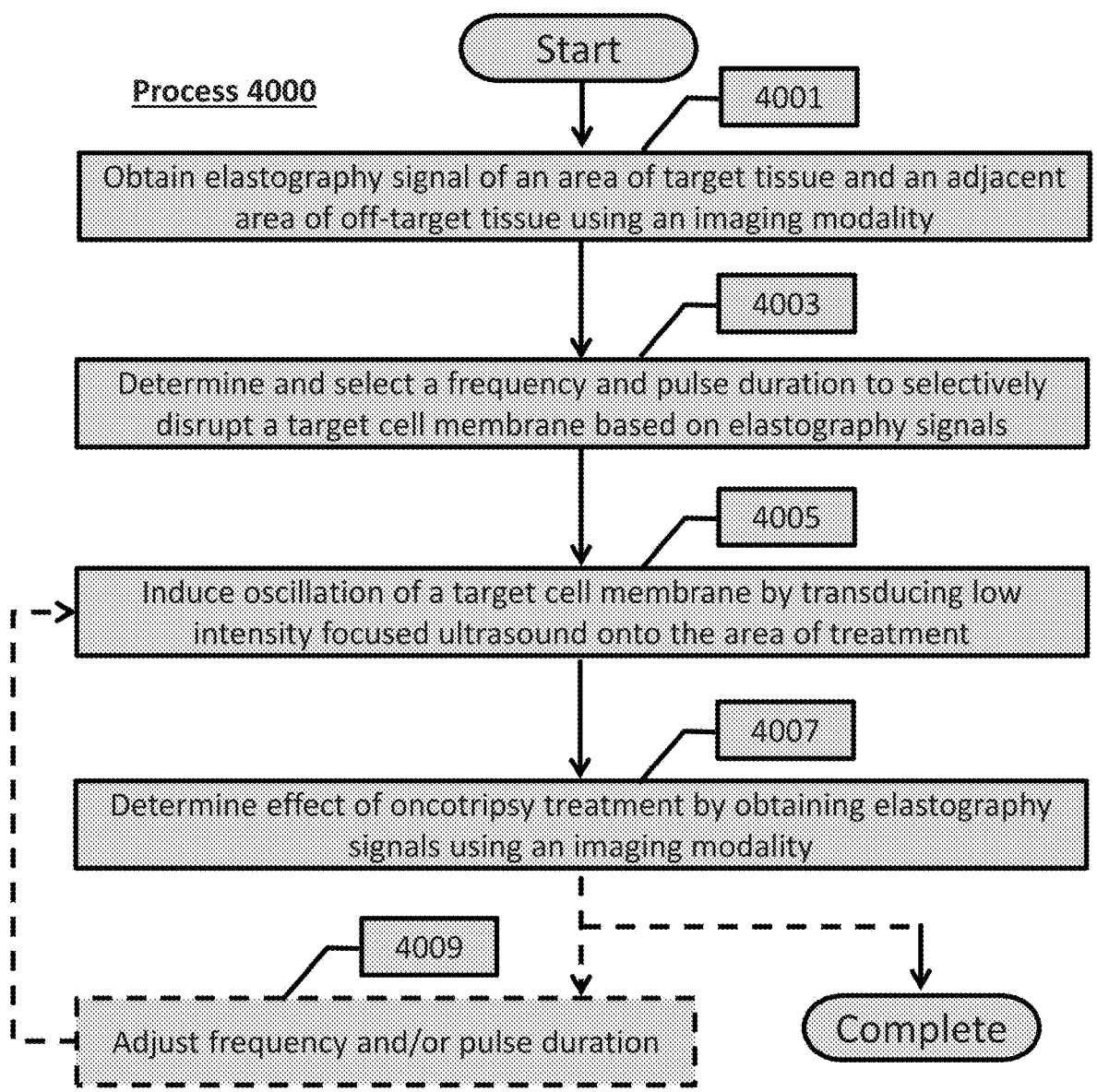

SELECTIVE DISRUPTION OF NEOPLASTIC CELLS VIA RESONANT HARMONIC EXCITATION

STATEMENT OF RELATED APPLICATIONS

The current application claims priority to U.S. Provisional Application No. 62/466,591, filed Mar. 3, 2017, the disclosure of which is incorporated herein by reference.

FIELD OF THE INVENTION

The current description is directed to systems and methods for performing targeted cell lysis by resonant harmonic excitation.

BACKGROUND OF THE INVENTION

Harmonic excitation refers to a sinusoidal external force of a certain frequency applied to a system. One response of a system to harmonic excitation is resonance. Resonance occurs when the external excitation applied has the same frequency as the natural frequency of the system. It leads to large displacements and can cause a system fail structurally. One example of such a resonance occurs when a glass is broken via the application of an auditory harmonic excitation. Harmonic excitation also can occur in many other contexts.

SUMMARY OF THE INVENTION

In accordance with many embodiments, the disclosure is directed to systems and methods for selective targeting of specific cell types by application of low intensity ultrasound harmonic excitation at their resonance frequency.

Methods for performing oncotripsy in accordance with embodiments of the invention are disclosed. In one embodiment, a method identifies a target cell type in an organism and identifying at least one off-target cell type present in the organism in the vicinity of the target cell type. The method selects an ultrasound frequency and a pulse duration that critically disrupts the membranes of the target cells but not the off-target cells via harmonic excitation. The method also subjects at least one area of the organism containing target cells to a low intensity focused ultrasound transduction tuned to the selected frequency and pulse duration to induce target cell permeabilization or lysis.

In a further embodiment, the frequency is selected from a range of 100 kHz to 1 MHz.

In another embodiment, the pulse duration is selected from a range of 1 millisecond to 1 second.

In a still further embodiment, the at least one area of the organism also contains off-target cells.

In still another embodiment, the off-target cells are not permeabilized or lysed.

In a yet further embodiment, the at least one area of the organism is a margin of a tumor.

In yet another embodiment, the target cells are cells selected from the group of neoplastic cells, pathogenic cells, and fat cells.

In a further embodiment again, the method also surgically excises a mass of cells including target cells.

In another embodiment again, the method also administers a. immunotherapeutic agent.

In a further additional embodiment, the method also administers a chemotherapeutic agent.

In an embodiment, a method identifies an area of an organism having target tissue comprising target cells and an adjacent area of off-target tissue comprising off-target cells. The method determines, using an elastography imaging modality, mechanical properties of the target and off-target cells. The method selects an ultrasound frequency and a pulse duration that critically disrupts the membranes of the target cells but not the off-target cells via harmonic excitation. The mechanical properties of the target and off-target cells are used to select frequency and pulse duration. The method also subjects at least one area of the organism containing target cells to a low intensity focused ultrasound transduction tuned to the selected frequency and pulse duration to induce target cell permeabilization or lysis.

In a further embodiment, the elastography imaging modality is an imaging device selected from ultrasound elastography, ultrasound speckle tracking, and combined magnetic resonance imaging.

In another embodiment, the frequency is selected from a range of 100 kHz to 1 MHz.

In a still further embodiment, the pulse duration is selected from a range of 1 millisecond to 1 second.

In still another embodiment, the at least one area of the organism also contains off-target cells.

In a yet further embodiment, the at least one area of the organism is a margin of a tumor.

In yet another embodiment, the target cells are cells selected from the group of neoplastic cells, pathogenic cells, and fat cells.

In a further embodiment again, the method also surgically excises a mass of cells including target cells.

In another embodiment again, the method also administers a. immunotherapeutic agent.

In a further additional embodiment, the method also administers a chemotherapeutic agent.

In another additional embodiment, the method also assesses the permeability or lysis of target cells in the at least on area of the organism using the at least cell using the elastography imaging modality by determining mechanical properties of the target and off-target cells. The method adjusts the ultrasound frequency and the pulse duration that critically disrupts the membranes of the target cells but not the off-target cells via harmonic excitation based on the assessment of the lysis of target cells. The mechanical properties of the target and off-target cells are used to select frequency and pulse duration. The method subjects the at least one area of the organism containing target cells to a low intensity focused ultrasound transduction tuned to the adjusted frequency and pulse duration to induce target cell permeabilization or lysis.

In a still yet further embodiment, the assessing and the adjusting is performed without user-intervention.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein:

FIG. 1A provides a schematic diagram of an oncotripsy mechanism to induce selective cellular lysis and death in accordance with embodiments.

FIG. 1B provides a schematic diagram of an oncotripsy mechanism working synergistically with immunotherapy and chemotherapy to induce selective cellular lysis and death in accordance with embodiments FIG. 2A provides a schematic diagram of a system for application of an ultrasonic harmonic excitation in accordance with embodiments.

FIG. 3 provides a flowchart of a method for performing oncotripsy, in accordance with embodiments.

FIG. 4 provides a flowchart of a method for performing oncotripsy in conjunction with elastography imaging, in accordance with embodiments FIG. 5 provides a conceptual graph of how to identify a selective target frequency to disrupt targeted cells in accordance with embodiments.

DETAILED DESCRIPTION OF THE INVENTION

Figure 2A:
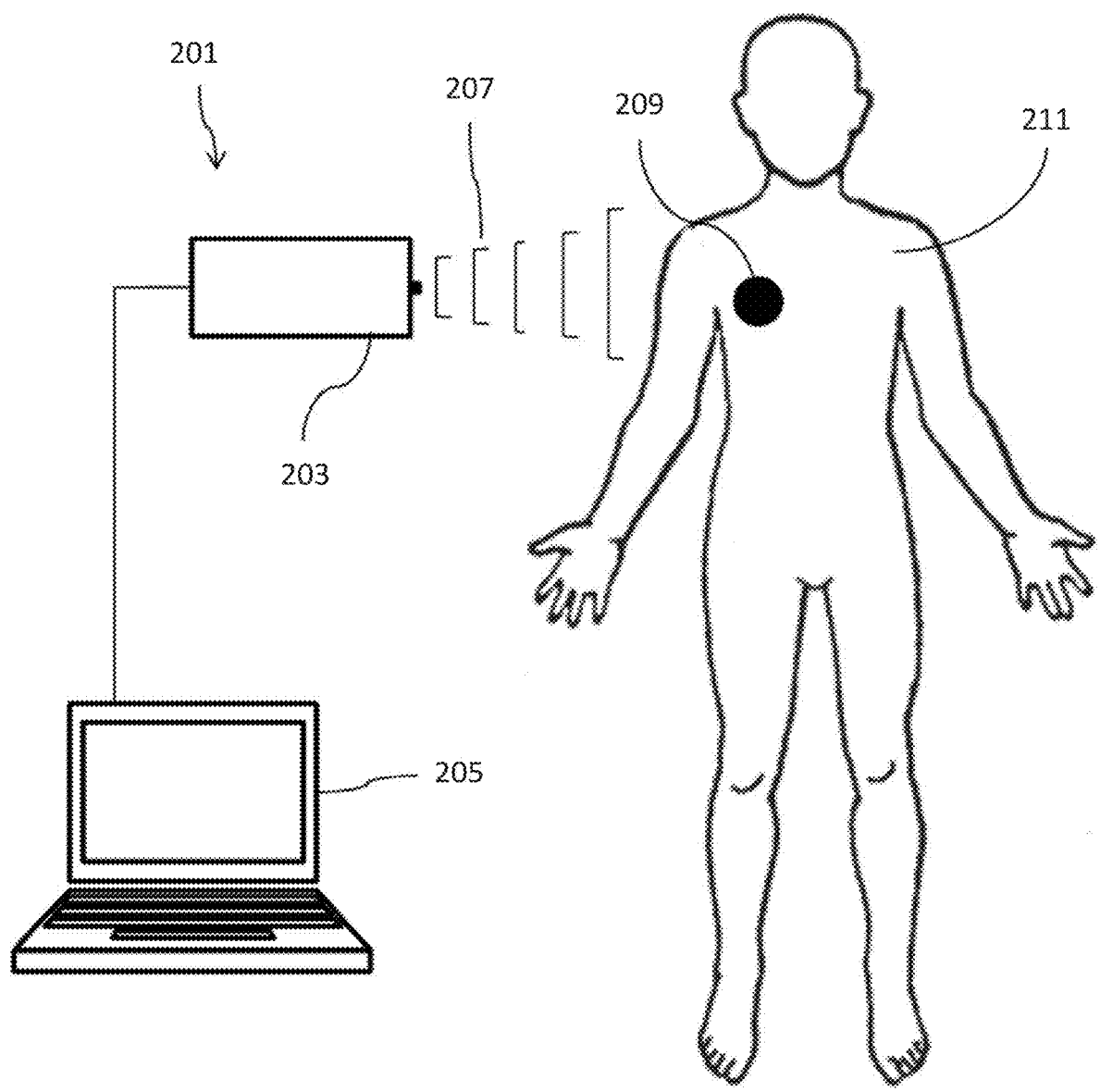
FIG. 2B provides a schematic diagram of a system for target cell imaging and application of an ultrasonic harmonic excitation in accordance with embodiments.

Turning to the drawings and detailed description, systems and methods for targeting specific cell types by selective application of ultrasonic harmonic excitation at their resonance frequency are described, such methods and systems maybe be referred to as "oncotripsy" hereinafter. In many embodiments, the systems and methods result in the disruption of targeted cell's membranes and potentially cell lysis by using ultrasonic harmonic excitations that have been specifically tuned to induce a destructive vibrational response therein while leaving non-targeted cell types intact. In various such embodiments the target cells types are neoplastic cells. Numerous embodiments described herein employ oncotripsy systems utilizing low intensity focused ultrasound (LIFU).

Oncotripsy can be utilized in a variety of the methods to selectively target and lyse various particular cell types. Selective oncotripsy, in accordance with a number of embodiments, exploits inherent structural differences between cell types, which in turn corresponds to a particular resonant response to selectively disrupt membrane structures of target cells without having a deleterious effect on nearby off-target cells. In many embodiments, an oncotripsy treatment, even when applied to tissue having target and off-target cell types, has a deleterious effect only on the targeted cells. Selective targeting can be achieved by tuning the frequency and pulse duration of ultrasound waves emitted from an oncotripsy system. In some embodiments, an effective oncotripsy frequency is selected from a range of 100 kHz to 1 MHz. In several embodiments, an effective oncotripsy pulse duration is selected from a range of 1 ms to 1 s.

Embodiments of therapeutic oncotripsy devices as described herein may be coupled with an imaging device designed to interrogate cells of interest to determine the optimum ultrasound parameters to induce targeted cell killing. In several embodiments, an elastography imaging modality is used to determine and differentiate the mechanical properties of target and off-target cells. Thus many embodiments utilize data derived from an acquired elastography image to determine an appropriate frequency and pulse duration to selectively target a particular cell type. In some embodiments, an elastography imaging modality works in concert with a of therapeutic oncotripsy device to yield a system capable of identifying and treating target cells with little to no user intervention.

Aberrations of Cellular Morphologies

Aberrations in both cellular morphology and material properties of different cell constituents are indications of various forms of neoplasms and cancerous tissues. For instance, a criterion for malignancy is the size difference between normal nuclei, with an average diameter of 7 to 9 microns, and malignant nuclei, which can reach a diameter of over 50 microns. (Berman, J. J., 2011. Precancer: The Beginning and the End of Cancer, 1st Edition. Jones & Bartlett Publishers, London, United Kingdom, the disclosure of which is incorporated herein by reference.) Early studies have shown that the nuclear-nucleolar volume ratios in normal tissues and benign as well as malignant tumors do not differ quantitatively. Nucleoli volumes of normal tissues, however, are found to be significantly smaller than the volume of nucleoli in cancerous tissues. (See, e.g., Guttman, P. H., Halpern, S., 1935. *Am. J. Cancer,* 25, 802-806, the disclosure of which is incorporated herein by reference.) Similarly, the mechanical stiffness of various cell components has been found to vary significantly in healthy and diseased tissues. The stiffness of live metastatic cancer cells was also investigated using atomic force microscopy, showing that cancer cells are more than 80% softer than healthy cells. (See, e.g., Cross, S. E., et al., 2007. *Nature Nanotechnology* 2, 780-783, the disclosure of which is incorporated herein by reference.) Other cancer types, including lung, breast and pancreas cancer, display similar stiffness characteristics. Furthermore, using a magnetic tweezers, it has been found that cancer cells with the lowest invasion and migratory potential are five times stiffer than cancer cells with the highest potential. (See, e.g., Swaminathan, et al., 2011. *Cancer Research* 71 (15), 5075-5080, the disclosure of which is incorporated herein by reference.) Likewise, increasing stiffness of the extracellular matrix (ECM) was reported to promote hepatocellular carcinoma (HCC) cell proliferation, thus being a strong predictor for HCC development. (See, e.g., Schrader, J., et al., 2011. *Hepatology* 53 (4), 1192-1205, the disclosure of which is incorporated herein by reference.) Moreover, enhanced cell contractility due to increased matrix stiffness results in an enhanced transformation of mammary epithelial cells. (See, e.g., Paszek, M. J., et al., 2005. *Cancer Cell* 8, 241-254, the disclosure of which is incorporated herein by reference.) Conversely, a decrease in tissue stiffness has been found to impede malignant growth in a murine model of breast cancer. (See, e.g., Levental, K. R., Y et al., 2009. *Cell* 139, 891-906, the disclosure of which is incorporated herein by reference.)

Various experimental techniques have been utilized in order to quantitatively assess the material properties of individual cell constituents in both healthy and diseased tissues. The inhomogeneity in stiffness of the living cell nucleus in normal human osteoblasts has been investigated using a noninvasive sensing system. (See, e.g., Konno, K., et al., 2013. *IFMBE Proceedings*. Vol. 39. Springer, pp. 290-293, the disclosure of which is incorporated herein by reference.) In such studies, the stiffness of the nucleolus is found to be relatively higher compared to that of other nuclear domains. Similarly, a difference in mass density between nucleolus and nucleoplasm in the *xenopus* oocyte nucleus has also been determined by recourse to refractive indices. (See, e.g., Handwerger, K. E., et al., 2005. *Mol Biol Cell* 16 (1), 202-211, the disclosure of which is incorporated herein by reference.) The elastic modulus of both isolated chromosomes and entire nuclei in epithelial cells have also been determined. Specifically, it has been shown that mitotic chromosomes behave linear elastically up to 200% extension. (See, e.g., Houchmandzadeh, B., et al., 1997. *J. Cell Biol.* 139, 1-12, the disclosure of which is incorporated herein by reference.) Experiments additionally measured the network elastic modulus of the nuclear envelope, independently of the nucleoplasm, by means of micropipette aspiration, suggesting that the nuclear envelope is much stiffer and stronger than the plasma membranes of cells. (See, e.g., Dahl, K. N., et al., 2004. *Journal of Cell Science* 117, 4779-4786, the disclosure of which is incorporated herein by reference.) In addition, wrinkling phenomena near the entrance of the micropipette were indicative of the solid-like behavior of the envelope. The elastic moduli of both cytoplasm and nucleus of hepatocellular carcinoma cells was also estimated based on force-displacement curves obtained from atomic force microscopy. (See, e.g., Kim, Y., et al., 2011. *Med. Biol. Engineering and Computing* 49 (4), 453-462, the disclosure of which is incorporated herein by reference.) In addition, micropipette aspiration techniques have been used in order to further elucidate the viscoelastic behavior of human hepatocytes and hepatocellular carcinoma cells. Based on these studies, it has been concluded that a change in the viscoelastic properties of cancer cells could affect metastasis and tumor cell invasion. (See, e.g., Zhang, G., et al., 2002. *World Journal of Gastroenterology* 8 (2), 243-246, the disclosure of which is incorporated herein by reference.) The increased compliance of cancerous and pre-cancerous cells was also investigated using atomic force microscopy to determine the mechanical stiffness of normal, metaplastic and dysplastic cells, showing a decrease in Young's modulus from normal to cancerous cells. (See, e.g., Fuhrmann, A., et al., 2011. *Physical Biology* 8, 1-10, the disclosure of which is incorporated herein by reference.)

A large body of literature has been also devoted to the investigation of the effects of carefully tuned ultrasound pulses on sonoporation, i.e., the formation of temporary pores in the cell membrane, and on enhanced endocytosis. (See, e.g., Lentacker, I., et al., 2014. *Advanced Drug Delivery Reviews* 72, 49-64, the disclosure of which is incorporated herein by reference.) Microbubble-assisted ultrasound has been shown to facilitate drug delivery, e. g., for enhancing the transport of chemotherapeutic agents into living cells. (See, e.g., Lammertink, B. H. A., et al., 2015. *Frontiers in Pharmacology* 6 (138), the disclosure of which is incorporated herein by reference.) The underlying biophysical mechanisms leading to an enhanced membrane permeability of cells are shear stresses induced by oscillating microbubbles, in the case of stable cavitation, and shock waves generated during microbubble collapse, in the case of inertial cavitation. (See, Lentacker, cited above).

Embodiments herein recognize that, the distinctive physical properties of different cell types provides a pathway for selectively targeting different cell types, and systems and methods are provided that utilize ultrasound harmonic excitation to induce resonant response of cells to selectively induce membrane disruption in selected cells, such as, for example, cancer cells.

Mechanistic Action of Selective Oncotripsy

Selective oncotripsy, as described in various embodiments herein, relies on the differences of mechanical properties between target and off-target cells. The differences of mechanical properties result in target cells having an inherent resonant response that is distinctive from the off-target cells. Selective oncotripsy, in accordance with a number of embodiments, exploits this difference in inherent resonant response to selectively disrupt the membrane structure of target cells without having a deleterious effect on the nearby off-target cells.

Often, target and off-target cells are comingled within a biological tissue, which creates a difficult environment for detection, medical intervention and treatment. This heterogeneity is common in a number of neoplasms and cancers, wherein neoplastic cells are co-mingled with healthy cells, especially at the margins of tumors and sites of metastasis. When using standard methods of treatment, such as surgical removal and high intensity focused ultrasound (HIFU), the comingling of target and off-target cells requires a determination to either remove/ablate healthy off-target cells along with the target cells or spare the healthy tissue and leave the target cells comingled within. This decision is especially critical in a number of cancers that arise in vital tissue, such as glioblastoma multiforme (GBM).

Clinical trials have demonstrated that high intensity focused ultrasound (HIFU) can improve clinical outcomes in prostate, breast, liver, pancreas, bone, and brain tumors (Y. H. Hsiao, et al. *J. Cancer* 2016, 7, 225-31; and D. S. Hersh, et al., *Neurosurgery* 2016, 79, 643-54; the disclosures of which are incorporated herein by reference). HIFU has a direct cyto-disruptive effect, and can also improve treatment of cancerous cells by increasing uptake of chemotherapeutics allowing for lower dosages of toxic drugs (M. Zhang, et al., *J. Ultrasound Med.* 215, 34, 435-40; and O. Couture, et al., *Translational Cancer Research* 2014, 3, 494-511; the disclosures of which are incorporated herein by reference) and releasing cancer cell antigens inducing a systemic anti-neoplastic immune response (J. Unga and M. Hashida *Adv. Drug Deliv. Rev.* 2014, 72, 144-53, the disclosure of which is incorporated herein by reference). However, HIFU's mechanism of action involves thermal ablation or acoustic cavitation that destroys tissue in a target area and as such is largely non-specific (J. F. Aubry, et al., *J. Ther. Ultrasound* 2013, 1, 13; and J. P. McGahan, et al., *J. Vasc. Interv. Radiol.* 1992, 3, 291-97; the disclosures of which are incorporated herein by reference). Safely implementing HIFU is an involved procedure that demands costly MRI tumor tracking to prevent off-target ablation and still may induce collateral damage (G. Malietzis, et al., *Br. J. Radiol.* 2013, 86, 20130044, the disclosure of which is incorporated herein by reference).

In contrast, ultrasound oncotripsy does not require tumor tracking or the enforcement of therapeutic margins. By taking advantage of its target cell selective mechanism, an oncotripsy system administers therapy to an entire organ and only disrupts targeted cells (e.g., neoplastic cells). This provides clinicians with a powerful and novel therapeutic technique to locally administer targeted cancer therapy without harming healthy tissue. Targeted tissues that differ in mechanical properties of stiffness or structure from surrounding healthy tissue are candidates for oncotripsy therapy.

Many of the most therapeutically challenging cancers involve a solid tumor mass with poorly defined borders and invasion into healthy tissue (B. A. Teicher *Oncol. Rep.* 2013, 30, 1030-34, the disclosure of which is incorporated herein by reference). While HIFU may be unable to safely ablate these tumors, oncotripsy's mechanism is specifically suited to target invading cells. For example, the treatment of GBM, the most common primary brain tumor in adults, is a massive challenge in neuro-oncology due to the difficulty of establishing effective surgical margins in brain tissue (D. Kondziolka, et al., *Neuro. Oncol.* 2015, 17, 29-44; and O. Cohen-Inbar, Z. Xu, and J. P. Sheehan, *J. Ther. Ultrasound* 2016, 4, 2; the disclosures of which are incorporated herein by reference). The shear elastic moduli is substantially different between normal brain tissue and glioma tissues (K. Pogoda, et al., *New J. Phys.,* 2014, 16, 075002, the disclosure of which is incorporated herein by reference), suggesting that oncotripsy may be a therapy to noninvasively destroy GBM. Similar applications for oncotripsy can be observed in liver and breast cancer. The liver is the second most common site for tumor metastases and the site of hepatocellular carcinoma (HCC), the fifth most common malignancy. Current standard of care is surgical resection or transplantation with ablation therapies used as a recourse. However, common liver metastases and HCC have a significantly different elastic moduli than normal liver parenchyma, making them an ideal potential candidate for oncotripsy therapy. Breast cancer is the leading cause of death among solid tumors in women, the most lethal phenotypes are highly invasive, and similar evidence exists of a cellular mechanical property mismatch between normal and metastatic cancer breast cells suggesting an application for oncotripsy.

Accordingly, there is a need for development of medical treatments that can selectively ablate unhealthy cells that are comingled within healthy tissue, and especially vital tissue. In a number of embodiments, oncotripsy treatment, even when applied to a comingled tissue, only has a deleterious effect on target cells. In many of embodiments, oncotripsy results in specific ablation of the target cells.

Ultrasound oncotripsy, in accordance with multiple embodiments, is a therapeutic system that involves implementation of low intensity ultrasound (L. B. Feril Jr., et al., *J. Med. Ultrason* (2001) 2008, 35, 153-60, the disclosure of which is incorporated herein by reference) with a specialized wave-form to induce a cell-specific cyto-disruptive effect in cancer cells, reducing off-target cell death from therapeutic ultrasound. Embodiments of oncotripsy utilize a method that takes advantage of the fact that various cell types are vulnerable to ultrasound at specific frequencies by exploiting a cell's inherent resonant response. As resonance behavior is dependent on mechanical and structural properties, the differing micro-environment and cytoskeletal properties between healthy and aberrant tissues (e.g., cancerous tissue) would cause each to have distinct critical frequencies. When stimulated at these critical frequencies, cells experience a growing mechanical vibration in their plasma membranes that can lead to increased cell permeability, lysis, and/or death.

Various embodiments described herein employ oncotripsy systems utilizing low intensity focused ultrasound (LIFU) to selectively target aberrant cell populations. Computational simulations and experimental data suggest that ultrasound waves at target frequencies induce resonant oscillation in the membrane of target cells (For more on computational simulations, see U.S. patent application Ser. No. 15/373,916 "Targeting Cancer Cells Via Resonant Harmonic Excitation," which is herein incorporated by reference in its entirety). Ultrasound oncotripsy involves applying these waves to harm aberrant cells without affecting healthy cells. Accordingly, a number of embodiments utilize oncotripsy to provide a safer and more versatile ultrasound cancer therapy.

Depicted in FIG. 1A is a mechanistic application of an oncotripsy treatment using LIFU (101). LIFU (101) is applied to a tissue (103) having a comingling of target cells (105) and off-target cells (107). The application of LIFU (101) results in specific ablation (109) of target cells (105) without a deleterious effect on off-target cells (107). In many embodiments, the LIFU is applied to a heterogeneous biological tissue having aberrant target and off-target healthy cells. In several embodiments, the target cells are neoplastic. The biological tissue to be treated, in accordance with several embodiments, is a margin of tumor growth or a site of metastasis.

Emerging protocols for cancer therapy are increasingly using synergistic therapy involving chemotherapeutics, immunotherapy, and surgery. Novel immunotherapy drugs that assist in the formation of a systemic anti-neoplastic immune response, such as anti-PD1 or TLR9 agents are showing promise in tumor remission and prevention of recurrence (M. T. Silvestrini et al., *JCI Insight* 2017, 2, e90521, the disclosure of which is incorporated herein by reference). Ultrasound oncotripsy can synergistically work with immunotherapy and/or chemotherapy to selectively increase the membrane permeability of target cells. This can allow for increased uptake of a chemotherapeutic or release tumor-specific antigen to induce a systemic anti-cancer immune response.

Oncotripsy results in disruption of the cellular membrane, which can lead to lysis of a target cell. Alternatively, disruption of the cellular membrane may not lead to lysis but it can permeabilize the membrane of a target cell, allowing for various molecules to flow into and out of the cell. Various embodiments can take advantage these mechanisms to better enhance treatment of target cells. Depicted in FIG. 1B is a mechanistic application of an oncotripsy treatment in combination with immunotherapies and chemotherapies. In accordance with various embodiments, LIFU is used to permeabilize and/or lyse target cells to enhance immunotherapeutic and/or chemotherapeutic treatment against the target cells.

Oncotripsy treatment used in combination with immunotherapy, in accordance with a number of embodiments, can lyse or permeabilize a target cell, releasing its contents. The target cell contents include various target-specific antigens, especially neoantigens in neoplastic cells. The host's immune system can be stimulated by a number methods and molecules, including cytokines (e.g., interleukin 2), interferons ($\alpha$, $\beta$, $\gamma$), and other drugs that provide an elevated immune response. Stimulation of the immune system increases immunosurveillance, including production of more antigen presenting cells (See, FIG. 1B). Oncotripsy treatment releases target-cell specific antigens, which can be surveyed by circulating antigen presenting cells. The antigen presenting cells can then communicate with cytotoxic T-cells to initiate an immunogenic response against antigen harboring target cells (See, FIG. 1B). This immunogenic response would specifically remove target cells systemically throughout the host's body, including tissue remote from the site of oncotripsy treatment. Accordingly, a subject may be administered an immunotherapeutic agent in conjunction with an oncotripsy treatment. Although a few immunotherapeutic agents are discussed, many more are known in the art and can be used in conjunction with oncotripsy treatments, in accordance of a multitude of embodiments.

Oncotripsy treatment can also be used in combination with chemotherapy, in accordance with various embodiments. Because oncotripsy treatment can induce selective permeabilization of target cells, the efficacy of chemotherapeutic reagents can be enhanced when used in combination (See, FIG. 1B). Accordingly, lower doses of chemotherapeutics could be used to achieve similar efficacy, reducing the side effects of chemotherapy and enhancing patient experience. Many chemotherapeutic agents are well known in the art, such as anthracyclines and taxanes for example, and thus many chemotherapeutic agents can be administered in conjunction with oncotripsy treatments, in accordance with a number of embodiments.

Systems for Performing Oncotripsy

The therapeutic technology of ultrasound oncotripsy, in accordance to various embodiments, involves using specifically targeted low intensity ultrasound waveforms to selectively induce cell disruption (including increased vulnerability to adjuvant therapies such as immunotherapy, chemotherapy, etc.) or direct cell death in target cells without harming healthy cells. Oncotripsy is based on the principle that each cell has a resonant response to ultrasound at certain critical frequencies. When excited at these particular frequencies, cells undergo more energetic oscillations in response to ultrasound which can lead to exceeding maximum strain tolerances of the cell or causing chronic fatigue failure of the cell, leading to cell disruption. To take advantage of this phenomenon, numerous embodiments of ultrasound oncotripsy technology modulate the frequency and pulsing parameters to find a waveform that leads to disruption in the target cells without damaging healthy cells.

Turning now to systems for performing oncoptripsy in some exemplary embodiments, as shown in FIG. 2A, a system (201) generally includes a tunable source of ultrasonic transduction (203) in signal communication with a control system (205) that allows control of several parameters, including frequency and pulse duration, of the ultrasonic transduction (207) to be tuned over a desired range selected by the user. During operation, the ultrasonic transduction source would be placed into a suitable position relative to a target (e.g., neoplastic cells) (209) in a patient (211) and the harmonic excitation activated at an excitation frequency configured to selectively create destructive resonance within targeted cells at an appropriate pulse duration, resulting in selective permeabilization and/or lysis of the cells.

It will be understood that any suitable ultrasonic emitter and control system capable of selecting an excitation frequency and pulse duration suitable for inducing permeabilization and/or lysis within a target cell may be utilized in accordance with embodiments. For example, in many embodiments the system incorporates a commercial low frequency and low-intensity ultrasonic transducer and controller. In some such embodiments the transducers are selected having a broad range of parameters capable of being tuned to produce ultrasound pulses in the frequency range of approximately 100 kHz to 1 MHz, in pulse duration range of 1 ms to 1 s, an acoustic density in the range of less than 5 W/cm$^2$, and an output pressure around 0.5 to 1 MPa.

Although specific critical frequencies and pulse durations are described herein, the transient response of cells at resonance may additionally incorporate different types of excitations, as can be determined in accordance with a number of embodiments of the invention.

Embodiments of therapeutic oncotripsy devices as described herein may be coupled with an imaging device designed to interrogate cells of interest to determine the optimum ultrasound parameters to induce targeted cell killing. In several embodiments, interrogation is performed non-invasively (using a device that can evaluate the cells of interest in vivo) or on samples taken via biopsy or other methods (using a device that isolates the target sample ex vivo). Techniques such as ultrasound elastography, ultrasound speckle tracking, or combined magnetic resonance imaging (including diffusion weighted imaging or other sequences used to assess cell damage) may be utilized in accordance to many embodiments to interrogate the system of interest and determine its mechanical properties and cellular response to ultrasound. Various embodiments of systems function as an open loop control where the compare the mechanical properties of the target cell to a library of mechanical properties that have been previously evaluated to be vulnerable to specific ultrasound waveforms. It may also open as a closed loop control in which the ultrasound waveform suggested by the imaging system is automatically used with the therapeutic component, and subsequently the imaging system can utilize the results of this waveform to further fine-tune the ultrasound waveform.

Figure 2B:
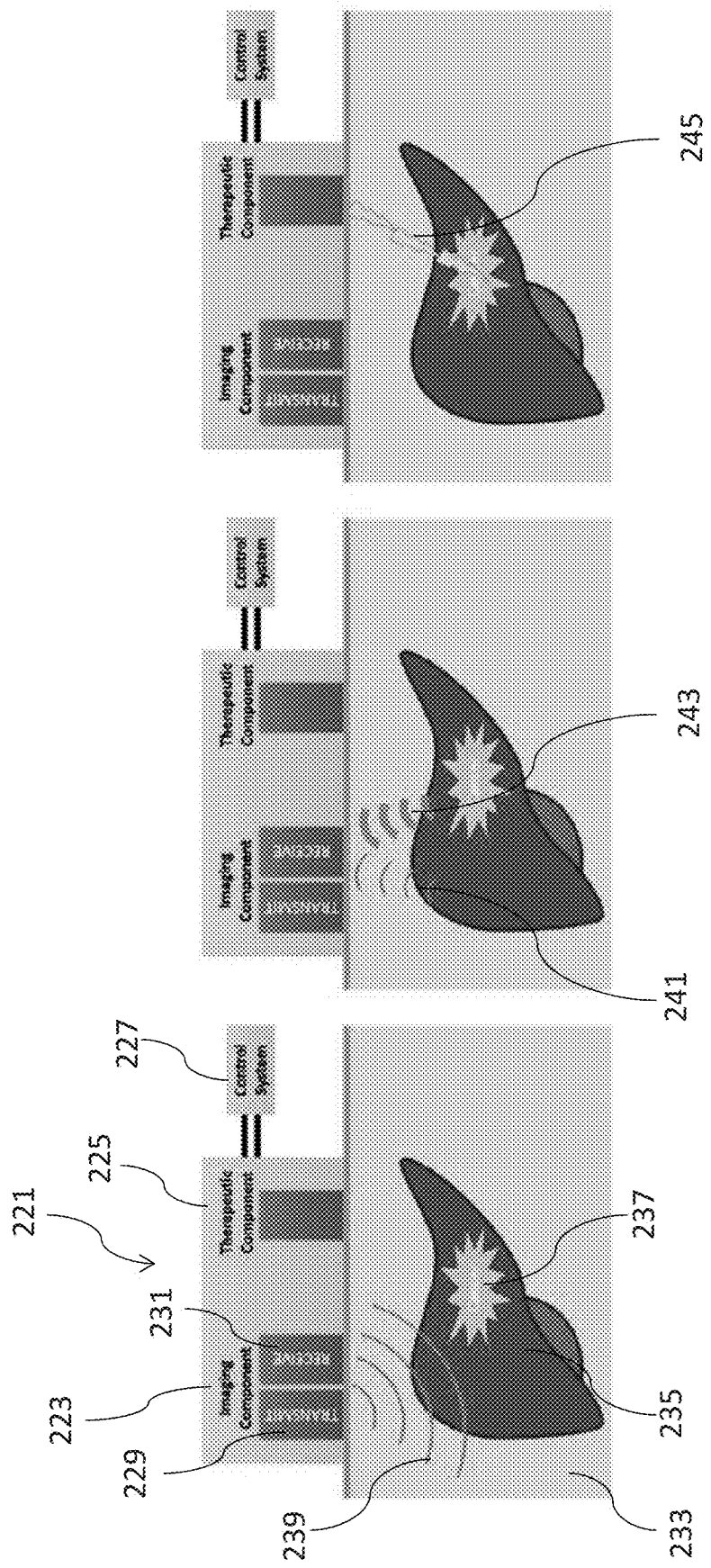

Depicted in FIG. 2B is an exemplary oncotripsy system (221) having an imaging component (223) working in conjunction with a therapeutic component (225) and connected to a control system (227) capable of controlling the imaging and therapeutic components. An imaging component (223) would typically include a signal transmitter (229) and a signal receiver (231), such that when situated near the body (233) of a subject, it is able to distinguish off-target tissue (235) from target tissue (237). The transmitter (229) sends out a signal (239), which is returned to the receiver (231). Return signals (241) from off-target tissue and return signals (243) from target tissue are detected and differentiated by the imaging component (223) to specifically identify cells to be targeted (237). During operation, the therapeutic component (225) would be placed into a suitable position relative to a target (e.g., neoplastic cells) (245) and emits LIFU to generated harmonic excitation at an excitation frequency with an appropriate pulse duration configured to selectively create destructive resonance within targeted cells, resulting in cell permeabilization, lysis, and/or death of the cells.

In accordance with a number of embodiments, an oncotripsy system, can implement various components to ensure proper detection and treatment of target cells. In many embodiments, a user is able to control the imaging component and therapeutic components. In some embodiments, imaging and therapeutic components work in concert to detect and treat target cells. Accordingly, in a number of embodiments, an imaging component can automatically determine an appropriate frequency and pulse duration for a therapeutic component to utilize. It should be understood that a number of imaging components capable of distinguishing target cells from off-target cells can be utilized in accordance with a number of embodiments.

Several embodiments of an oncotripsy system incorporate an elastography imaging system to detect and distinguish target cells from off-target cells. Elastography imaging is a technique capable of determining mechanical properties, such as rigidity and stiffness, of a detected tissue. Accordingly, in numerous embodiments, an elastography imaging system is capable of detecting the mechanical properties of target and off-target cells. The differences of mechanical properties can be used to fine tune a therapeutic component to determine an appropriate frequency and pulse duration that would have a therapeutic effect on target cells but have little to no detrimental effect on off-target cells. Examples of elastography imaging systems that can be incorporated into a therapeutic oncotripsy system include ultrasound and MRI elastography.

Numerous embodiments of systems of oncotripsy treatment have a variety of applications, especially in cancer therapy, where cancerous cells may be comingled with healthy cells, and thus a targeted ultrasound therapy can increase safety and efficacy over non-targeted US therapy. Various embodiments, however, also have applications in other fields such as microbiology (targeting pathogens such as bacteria, parasites, etc.), cosmetic surgery (targeting fat cells, etc.), and a variety of other applications where targeting a cell based upon its mechanical properties may be desired. In the field of oncology, targeting a cell based on its mechanical property would represent a paradigm shift from the classical techniques of targeting a cell based on its location or its molecular markers.

Treatment Regimens Utilizing Oncotripsy

Various embodiments of oncotripsy systems can be utilized in a number of treatment regimens. In general, many embodiments of treatment regimens target a particular cell type to induce harmonic excitation of the cell type, leading to disruption of cellular membranes. The disruption increases cell permeability and cell lysis.

Depicted in FIG. 3 is an embodiment of a process to induce oscillation of a target cell utilizing an oncotripsy system. Process 3000 can begin with identifying (3001) an area for oncotripsy treatment. Typically, in accordance with multiple embodiments, an area for treatment is an area containing target cells. Cells to be targeted depend on the purpose of treatment. In many embodiments, aberrant neoplastic cells are targeted in an oncologic treatment. In some embodiments, parasitic cells are targeted in treatments for infectious disease. Embodiments also target undesired cells (e.g., fat cells) in a cosmetic treatment. It should be understood that number of areas could be treated in accordance with various embodiments wherein the treatment involves targeting cells within an area based upon their mechanical properties and resulting in selective disruption the targeted cells' membranes.

It should also be understood that because oncotripsy treatment has little to no detrimental effect on off-target cells, areas to be treated can be selected naively, in accordance with numerous embodiments, without concrete knowledge of target cells existing within the area. Naïve treatments of various areas may be beneficial when detection of target cells is difficult, cumbersome, or costly. Accordingly, in many embodiments, veiled target cells are treated without precise unveiling of their whereabouts.

Process 3000 selects (3003) a frequency and pulse duration to disrupt a target cell membrane. In many embodiments, the frequency is selected from a range of 100 kHz to 1 MHz and the pulse duration is selected from a range of 1 ms to 1 s. The appropriate frequency and pulse duration is dependent on the critical frequency and pulse duration to induce oscillation of the target cell, disrupting its membrane. Several embodiments are also directed to selecting an appropriate frequency and pulse duration that has little to no disruptive effect on off-target cells. A cell's mechanical properties, including rigidity and stiffness, can alter a cell's harmonic response to ultrasound excitation. Accordingly, the appropriate frequency and pulse duration to selectively disrupt target cells can be determined by the target cell's mechanical properties. In a number of embodiments, the differences between the mechanical properties of a target cell and off-target cell are utilized to determine an appropriate frequency and pulse duration.

Utilizing the selected frequency and pulse duration, process 3000 induces (3005) oscillation of a target cell membrane by transducing LIFU on the area treatment. In several embodiments, the induced oscillations disrupt the target cell's membrane, permeabilizing, lysing, and/or killing the cell. In numerous embodiments, the LIFU is emitted with an acoustic density in the range of less than 5 W/cm$^2$ and an output pressure around 0.5 to 1 MPa. It should be understood, however, the appropriate parameters can be altered dependent on the application and desired result.

While specific examples of processes to induce oscillation of a target cell are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of to induce oscillation of a target cell appropriate to the requirements of a given application can be utilized in accordance with various embodiments of the invention.

Depicted in FIG. 4 is a process to perform oncotripsy in conjunction with elastography imaging. Generally, embodiments utilize elastography to identify target cells for treatment, to provide mechanical data of the target and off-target cells, and to assess treatment in real-time. In some embodiments, the method can be performed in a closed-loop system, such that the elastography imager and LIFU transducer work in concert to identify target cells, determine appropriate parameters including frequency and pulse duration, transmit LIFU onto the target cells, assess the treatment, and adjust parameters as necessary with very little human intervention.

Process 4000 can begin by obtaining (4001) an elastography signal of an area of off-target tissue and an adjacent area of target tissue to determine their mechanical properties (e.g., rigidity). Several embodiments are directed to the use of ultrasound and/or MRI elastography imaging, however, any appropriate device capable of determining mechanical properties of the tissues can be used.

In many embodiments, the target tissue primarily contains cells to be targeted and the off-target tissue consists of primary off-target cells. For example, in some embodiments, the target tissue is a neoplastic growth or tumor and the off-target tissue is a collection of senescent cells typical of a healthy organ. The precise definition of target and off-target tissues will likely vary dependent on the application. Obtaining elastography signals of tissues consisting primarily of a particular cell type (e.g., target cells) ensures accurate mechanical readings related to that cell type.

When determining which tissues to obtain an elastography signal, in accordance with several embodiments, it is important to consider the area of treatment. In a number of embodiments, an area to be treated contains comingled target and off-target cells (e.g., margins of a tumor) and thus the appropriate tissue to perform elastography upon would be determined by the comingled cells in the area of treatment. For example, oncotripsy may be performed on the margins of a tumor that likely includes tumorigenic and healthy cells, and thus appropriate tissues to obtain mechanical properties would include the tumor (i.e., target) and the nearby healthy tissue (i.e., off-target) nearby the tumor.

Elastography signals can be used to determine and select (4003) a frequency and pulse duration to selectively disrupt membranes of the target cell membranes. The elastography signals should reveal the differential mechanical properties of the target and off-target cells. Accordingly, these differential mechanical properties can be used to select an appropriate frequency and pulse duration that disrupts the membranes of target cells but has little to no detrimental effect on off-target cells.

In a number of embodiments, the appropriate frequency and pulse duration is determined and selected by a doctor or technician reading the elastography output. In many embodiments, the appropriate frequency and pulse duration is determined and selected by the oncotripsy device itself, utilizing information stored within it to correlate the elastography reading with appropriate parameters for oncotripsy treatment.

Process 4000 induces (4005) oscillation of the membranes of target cells by transducing LIFU onto the area of treatment. In many embodiments, oscillation of the membranes of target cells results in permeability, lysis, and/or death of the cells. In several embodiments, the LIFU has a frequency and pulse duration to selectively disrupt the membranes of target cells but does not disrupt membranes of off-target cells. In numerous embodiments, LIFU is emitted with an acoustic density in the range of less than 5 W/cm$^2$ and an output pressure around 0.5 to 1 MPa. It should be understood however, the appropriate parameters can be altered dependent on the application and desired result.

Utilizing the elastography imaging modality, process 4000 determines (4007) the effect of oncotripsy treatment by obtaining elastography signals of the treated area. The elastography signals should indicate a status of mechanical properties of the treated area, which should change during treatment as targeted cells are lysed. Accordingly, the elastography signals should indicate whether a treated area still contains target cells. Utilizing the elastography signal data, treatments can be repeated and/or frequency and pulse duration adjusted (4009). In several embodiments, frequency and pulse duration are adjusted in real-time based on the elastography signal data without input from a user.

While specific examples of processes to perform oncotripsy in conjunction with elastography imaging are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of to perform oncotripsy in conjunction with elastography imaging appropriate to the requirements of a given application can be utilized in accordance with various embodiments of the invention.

A number of embodiments incorporate oncotripsy in a surgical procedure, such as those to remove a mass of cells (e.g., neoplastic cells, fat cells). Oncotripsy can be especially useful when target cells to be surgically removed are comingled with healthy tissue, making it difficult to remove these cells. This is common, for example, in surgeries to remove neoplastic tumors that do not have well defined margins (e.g., GBM). Accordingly, embodiments of methods involve oncotripsy in a combined therapeutic approach. Surgeons may ablate or resect the bulk of the tumor using traditional, minimally invasive, or non-invasive techniques. The tissue excised or destroyed through these techniques would be primarily cancer tissue without causing harm to a patient. Surgical techniques, however, may not be efficient alone, leaving behind many cancerous cells within various tissues, including the margins of resection, invaded nearby tissue, distant metastases, and/or regions that contain vital tissue. In many embodiments, oncotripsy can be performed around the excision site, and especially within the margins. In a number of embodiments, oncotripsy is performed upon the entire body to reach every tissue. In several embodiments, oncotripsy is performed during post-surgical follow up procedures. Oncotripsy may be performed non-invasively from outside the body, or applied using minimally invasive or traditional surgical access points generated during surgery.

Many embodiments are also directed to combining immunotherapy with oncotripsy. Immunotherapy is an emerging treatment in cancer therapy. The basic principle of immunotherapy is to enhance the host's immune response so that it can recognize and remove neoplastic cells throughout the body. Because oncotripsy can cause permeability, lysis, and/or death of a target cell, neoantigens within targeted neoplastic cells can be released by oncotripsy treatment. As such, oncotripsy can further boost an immune response against target cells as these antigens will be recognized by the immune system to stimulate a systemic response against neoplastic cells. Accordingly, in several embodiments, a host can be treated with an immunotherapeutic reagent such as anti-PD1, TLR9 agents, etc., in conjunction with oncotripsy to enhance immune activation to the released antigens from an oncotripsy treatment.

In accordance with numerous embodiments, oncotripsy is combined with chemotherapy. Chemotherapy is a common treatment for various neoplasms and cancers, but often requires a dose having severe side effects resulting in an unpleasant experience for the patient. Oncotripsy can be coupled with chemotherapy to reduce the effective amount of chemotherapeutic dose required to achieve the desired result. Because oncotripsy permeabilizes target cells, chemotherapeutic reagents can more easily access targeted neoplastic cells and kill them. Accordingly, many embodiments treat an individual with a chemotherapeutic reagent and subsequently treat the individual with oncotripsy. It should be understood that any chemotherapeutic reagent could be used in accordance with several embodiments, and a number of chemotherapeutic reagents are known in the art.

Numerous embodiments also utilize in oncotripsy in a device capable of metastatic surveillance. Accordingly, in some embodiments, an oncotripsy system is built into an implantable or wearable device that can be situated within or on a subject such that the oncotripsy can survey cells traveling through the blood or lymphatic system. Various embodiments of surveillance oncotripsy systems utilize an elastography imaging system to determine which cells are abnormal, signaling the system to selectively induce oncotripsy on target cells to induce their lysis and/or death. For example, an oncotripsy system may be situated at a vein or lymphatic drainage duct leaving an area that may be a source of metastatic spread. Oncotripsy could then be applied continuously in a manner that metastatic or invading tumor cells would be destroyed before they had the chance to cause tumor progression. This technique could also be applied, in accordance of multiple embodiments, in common veins such as the vena cava or common lymphatic trunks, to destroy tumor cells released from multiple tumor locations within the body.

Selection of Critical Frequency and Pulse for Cell Targeting

A number of embodiments are directed to methods for performing oncotripsy that include determining an excitation range (frequency and pulse duration) that will allow for the selective use of harmonic excitation to induce permeability, lysis, and/or death of target cells (e.g., neoplastic cells), by tuned ultrasound harmonic excitation while simultaneously leaving normal cells intact, i.e., oncotripsy. Accordingly, in various embodiments the vibrational response of target and healthy cells can be used to allow one to choose the frequency and pulse duration of the harmonic excitation to induce lysis of membranes of target cells selectively such that no risk arises to the healthy cells.

Figure 5:
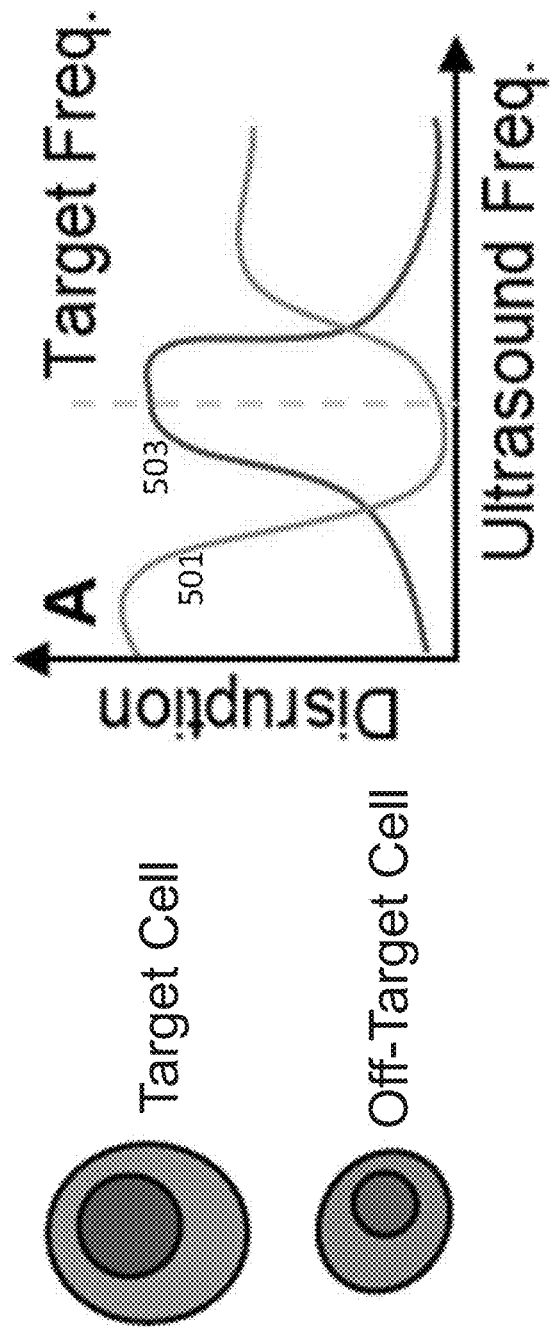

Many methods are available for determining appropriate oncotripsy conditions for a specific target cell type. Depicted in FIG. 5 is graphical representation on how to choose an excitation ultrasound frequency to induce membrane disruption in a target cell. Various cell types having unique structural constituents will have a unique set of critical ultrasound frequencies that render it vulnerable to harmonic excitation. At critical ultrasound frequencies, membranes of targeted cells oscillate, causing a disruption in membrane integrity leading to permeability, lysis, and/or death. As can be seen in FIG. 5, a target cell type (501) and off-target cell type (503) will each have a corresponding response to various frequencies. Each cell type will have a range of critical frequencies that can disrupt a cell's membrane and thus a target frequency can be selected that preferentially disrupts membranes of a targeted cell type and minimal disruption of off-target cell types. It should be understood that the precise range of target frequencies would depend on the cell type to be targeted and the off-target cells in the nearby surrounding area. Critical frequencies can be determined, in accordance with various embodiments by various experimental and/or computational methods. Computational methods to determine critical frequency are described in detail in U.S. patent application Ser. No. 15/373,916, cited supra.

Figure 6:
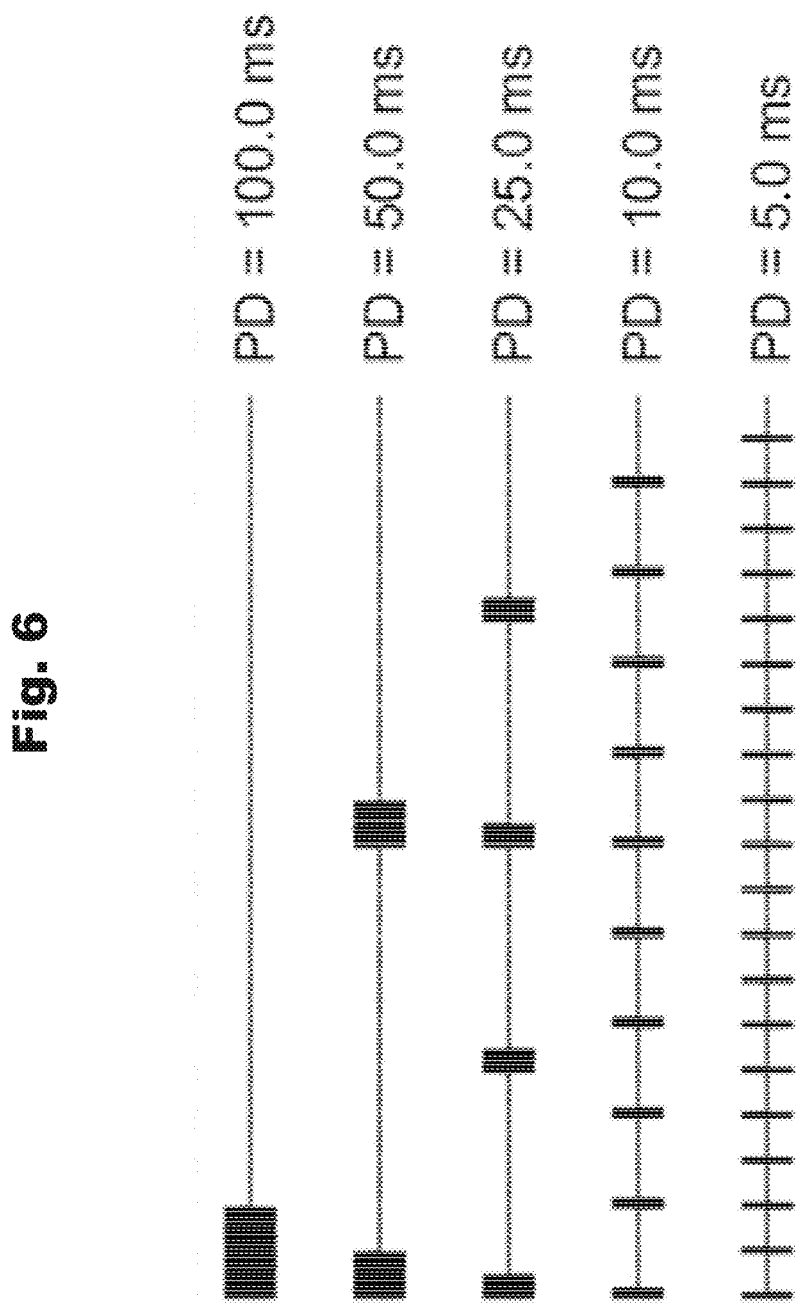
FIG. 6 provides a diagram of varying pulse duration (PD) in accordance with embodiments.
Figure 7:
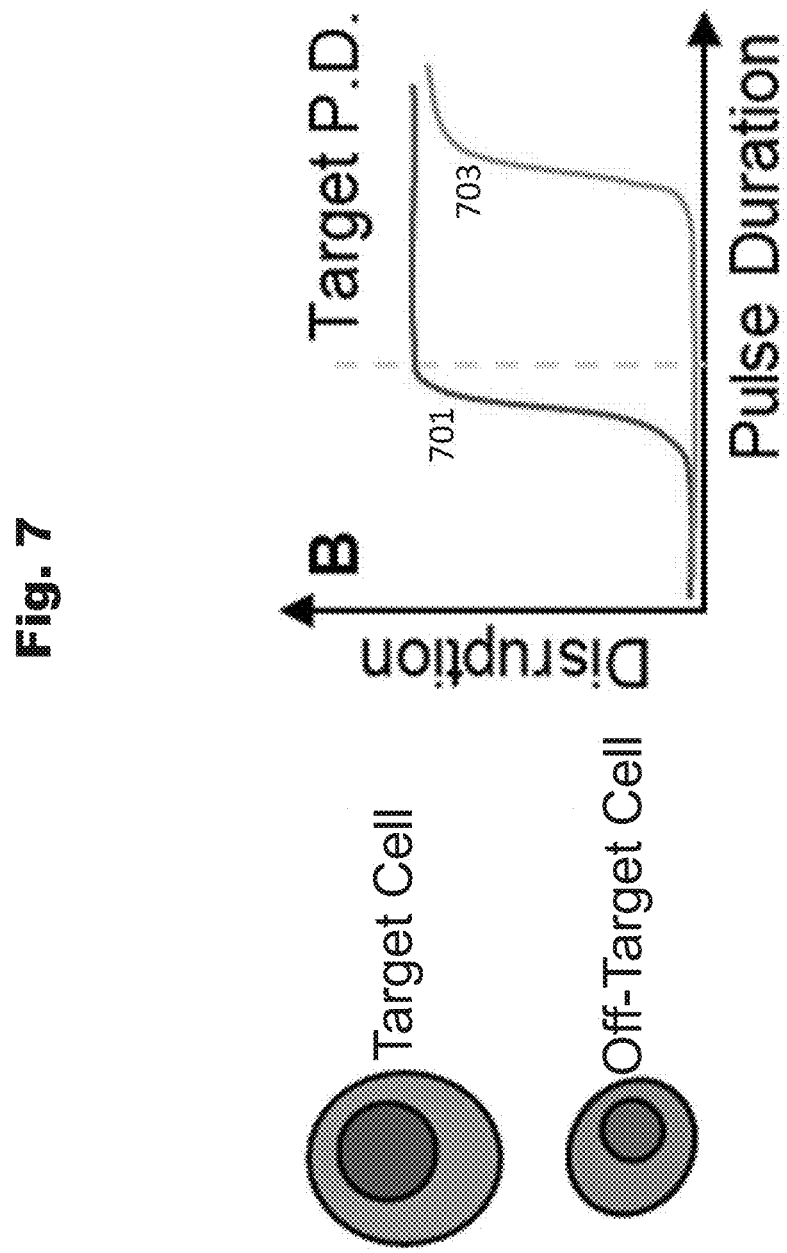
FIG. 7 provides a conceptual graph of how to identify a selective target pulse duration to disrupt targeted cells in accordance with embodiments.

In addition to frequency, various embodiments of an oncotripsy device control the pulsing parameters at which it emits ultrasound to further enhance the cell selectivity of membrane disruption in a target cell. Pulse duration is the length of time an ultrasound pulse is emitted. An oncotripsy device may change the pulse duration while varying the pulse repetition frequency such that the same ultrasound energy is deposited (see FIG. 6). Through this technique, the pulse duration can be configured to any defined value, including a range from 1 ms to 1 s. Oncotripsy devices induce selective cell death by applying ultrasound at the critical frequency of target cells, leading to larger oscillation growth rates in these cells in relation to off-target cells. By tuning the pulse duration, an oncotripsy device can apply sufficiently long pulses to cause target cells to undergo lysis, while the oscillations in off-target cells remain sub-critical. Depicted in FIG. 7 is a graphical representation of how pulse duration can be used to selectively disrupt a target cell. At the critical frequency for the target cells, various target cells (701) have a more sensitive response to shorter pulse durations than off-target cells (703), which would require longer pulse durations for disruption. Accordingly, in a number of embodiments, membranes of target cell type can be selectively disrupted from surrounding off-target cells by utilizing shorter pulse durations. In some embodiments, a pulse durations of less than 100, 50, 20, 10, 5, or 1 ms is selected and used to target cells (e.g., neoplastic cells). In various embodiments, short pulse durations used to target neoplastic cells have little to no disruptive effect on healthy off-target cells. It should be understood that effective pulse duration to selectively target cells can be determined experimentally or other methods understood in the art.

In many embodiments, critical ranges of frequency and pulse duration of a targeted cell type can be determined directly on the cell type utilizing an experimental approach. Accordingly, oncotripsy utilizing a range of frequencies and pulse durations can be performed on a particular cell type, quantifying the resulting permeability, lysis, and/or death. In several embodiments, experimental methods are performed on in vitro cells grown in culture that replicate a target cell type. For example, if a particular neoplastic cell is to be targeted, a cancerous in vitro cell line (e.g., K562 replicating leukemia) can be analyzed.

In numerous embodiments, an extracted biopsy from a patient is utilized to determine critical frequencies of cell types to be targeted. In many of these embodiments, a biopsy would have target cells and thus these target cells can be utilized to determine their critical ranges for ultrasound frequency and pulse duration. In some embodiments, an off-target biopsy can be excised, having healthy off-target cells, especially cells likely to be comingled with target cells at the target site, and these off-target cells can be used to help refine appropriate critical ranges that selectively disrupt target cells without having a significant disruptive effect on the off-target cells. In many embodiments, an extracted biopsy is utilized to determine a patient-specific therapy with unique critical ranges of frequency and pulse duration.

Various embodiments are also directed to building and establishing databases incorporating critical frequency and pulse duration parameters for a number of cell types, including target and off-target cells. These databases can be collected over time from a number of samples, derived from any appropriate source such as in vitro cell lines and patient biopsies. The database can be used to make determinations of which frequencies and pulse durations to utilize for a variety of oncotripsy methods.

Several embodiments incorporate noninvasive elastography imaging to determine critical ranges of frequency and pulse duration. Elastography imaging utilizing ultrasound and MRI can be used to determine the mechanical properties of tissues and cells. Accordingly, various embodiments utilize elastography imaging to determine the rigidity and stiffness of target and off-target cells to further determine an appropriate frequency and pulse duration to selectively disrupt the membranes of the target cells.

A number of embodiments utilize elastography imaging in a closed-loop process such that selection of frequency and pulse duration occur based on elastography images obtained with little to no user intervention. When elastography imaging is linked to an oncotripsy system, acquired elastography images can determine the various cell types present, the mechanical properties of the cell types, and appropriate ranges of critical frequencies and pulse duration. The revealed mechanical properties can be used to set parameters on an oncotripsy system. In some embodiments, parameters of an oncotripsy system are automatically selected based on mechanical property data. In several embodiments, parameters of an oncotripsy system are automatically updated in real-time based on real-time elastography imaging data.

EXEMPLARY EMBODIMENTS

In this section several examples of systems and methods for determining harmonic excitation frequencies and pulse duration for performing oncotripsy and for performing oncotripsy on target cells are provided. In addition, the performance of several embodiments of the systems and methods are provided. The person skilled in the art will recognize that additional embodiments according to the invention are contemplated as being within the scope of the foregoing generic disclosure, and no disclaimer is in any way intended by these non-limiting examples.

Example 1: Modulation of Frequency and Pulse Duration

Figure 8:
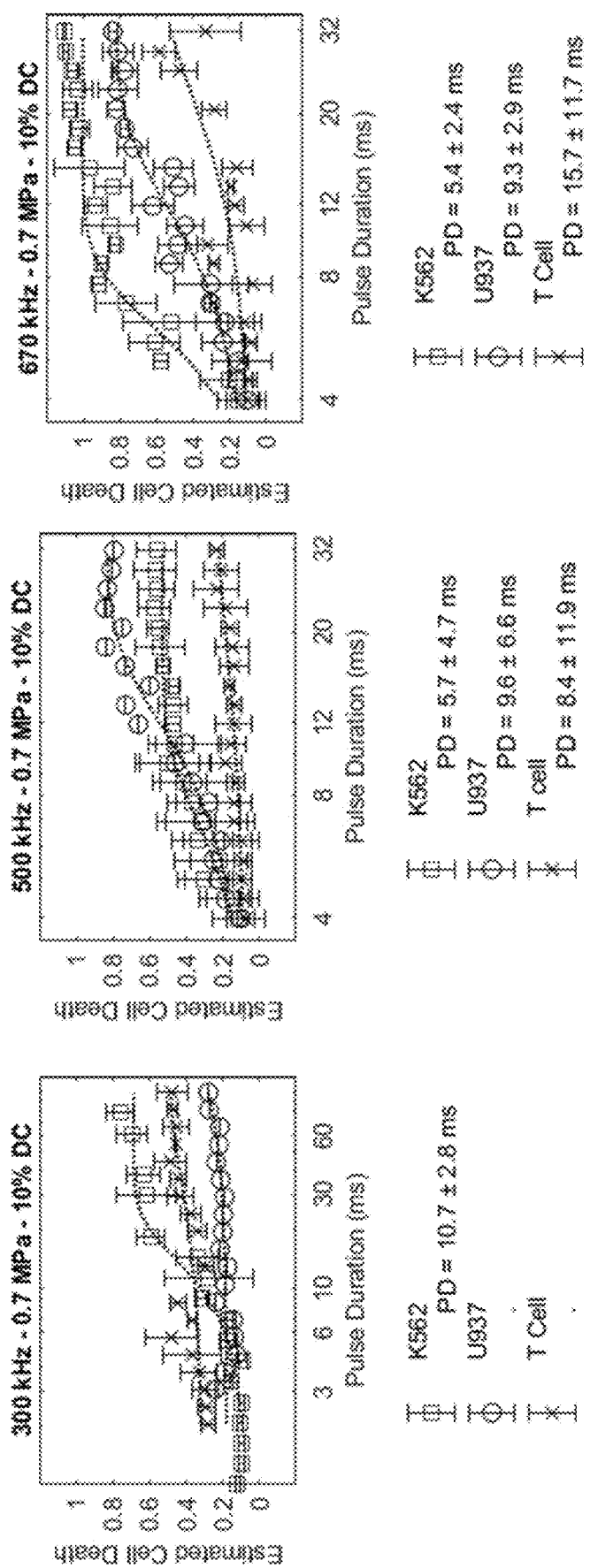
FIG. 8 provides three data graphs depicting the response of three cell lines to oncotripsy treatment at various frequencies and pulse durations, generated in accordance with embodiments.

Depicted in FIG. 8 are results of an experiment of performing oncotripsy on various cells in which the frequency and pulse duration has been modulated. Three cell types were used, two neoplastic cell types: leukemia derived K562 and U937 lines, and one control cell type of healthy T-cells. The three cell lines were exposed to oncotripsy at three frequencies (300, 500, and 670 kHz) and a range of pulse duration (approximately 1 ms to 100 ms) and their viability post-treatment was measured. The results from the experiment indicate that each cell line responds uniquely to the various frequencies. Notably, the control T-cell line did not appreciably respond to any of the frequencies tested. The two neoplastic lines, however, each responded to the 500 and 670 kHz frequencies resulting in high cell death. Also of note is that the two neoplastic lines had a greater response to shorter pulse durations than the control line, thus each having a lower critical pulse duration. Accordingly, these data show that at an appropriate frequency and pulse duration, targeted cells can be selectively disrupted, resulting in selective lysis and cell death.

Example 2: In Vivo Oncotripsy Results

Figure 9:
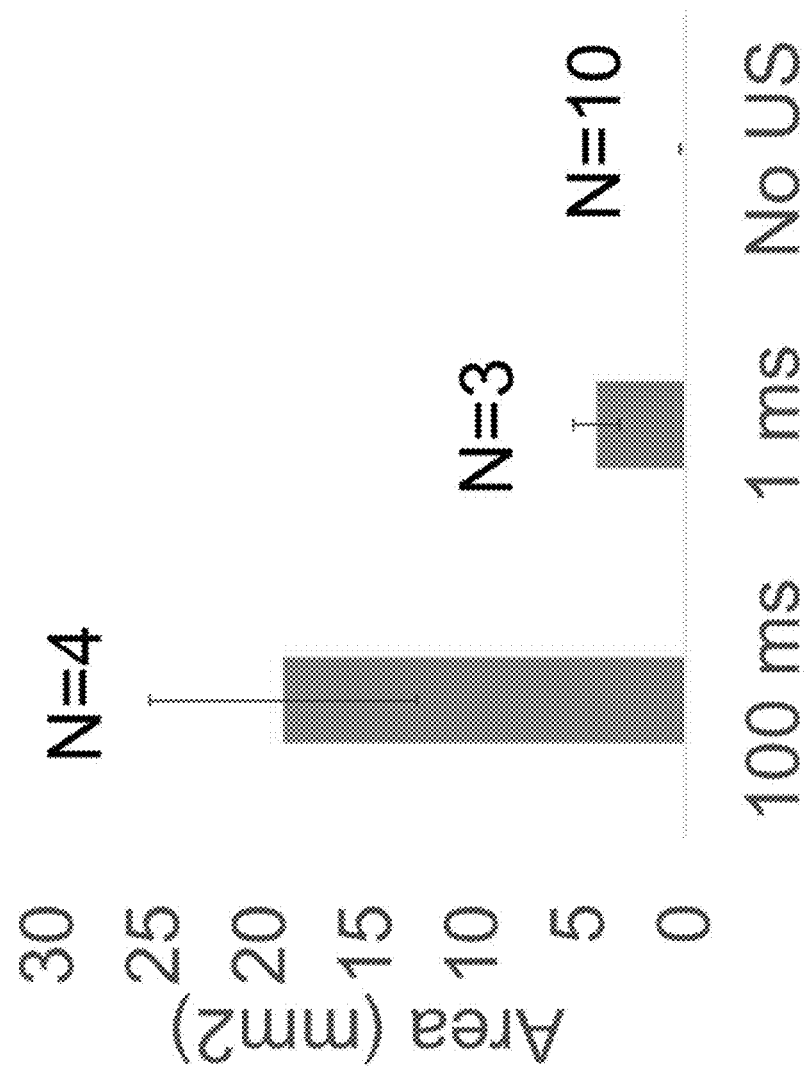
FIG. 9 provides a graph depicting necrotic lesions from an in vivo oncotripsy treatment, generated in accordance with embodiments.

Depicted in FIG. 9 are results from an in vivo oncotripsy experiment in which mice harboring tumors were treated, resulting in high levels of necrosis. Tumors were implanted subcutaneously of immunodeficient mice (NOD-SCID). The tumor area of a number of mice was treated with 670 kHz and either a pulse duration of 1 or 100 ms. As the results show, treatments with ultrasound induced necrosis with 100 ms pulse duration exhibiting greater necrosis. Control mice, which received no oncotripsy treatment, had no discernable necrosis. These data confirm that oncotripsy can be performed on subjects in vivo.

What is claimed is:

1. A method of performing oncotripsy comprising:
   identifying an area of an organism having target tissue comprising target cells and an adjacent area of off-target tissue comprising off-target cells;
   determining, using an elastography imaging modality, mechanical properties of the target cells and the off-target cells;
   selecting an ultrasound frequency and a pulse duration that critically disrupts membranes of the target cells but not the off-target cells via harmonic excitation, wherein the mechanical properties of the target cells and the off-target cells are used to select the frequency and the pulse duration;
   subjecting at least one region of the organism containing the target cells to a low intensity focused ultrasound transduction tuned to the selected frequency and the selected pulse duration to induce target cell permeabilization or lysis; and
   assessing the target cell permeabilization or the lysis of the target cells in the at least one region of the organism using the elastography imaging modality by determining mechanical properties of the target cells and the off-target cells.

2. The method of claim 1, wherein the elastography imaging modality is an imaging device selected from the group consisting of ultrasound elastography, ultrasound speckle tracking, and combined magnetic resonance imaging.

3. The method of claim 1, wherein the frequency is selected from a range of 100 kHz to 1 MHz.

4. The method of claim 1, wherein the pulse duration is selected from a range of 1 millisecond to 1 second.

5. The method of claim 1, wherein the at least one region of the organism also contains the off-target cells.

6. The method of claim 5, wherein the at least one region of the organism is a margin of a tumor.

7. The method of claim 1, wherein the target cells are cells selected from the group consisting of neoplastic cells, pathogenic cells, and fat cells.

8. The method of claim 1 further comprising surgically excising a mass of cells comprising the target cells.

9. The method of claim 1 further comprising administering an immunotherapeutic agent.

10. The method of claim 1 further comprising administering a chemotherapeutic agent.

11. The method of claim 1 further comprising:
   adjusting the ultrasound frequency and the pulse duration that critically disrupts the membranes of the target cells but not the off-target cells via harmonic excitation based on the assessment of the target cell permeabilization or the lysis of the target cells, wherein the mechanical properties of the target cells and the off-target cells are used to select the adjusted frequency and the adjusted pulse duration; and
   subjecting the at least one region of the organism containing the target cells to the low intensity focused ultrasound transduction tuned to the adjusted frequency and the adjusted pulse duration to induce the target cell permeabilization or the lysis of the target cells.

12. The method of claim 11, wherein the assessing and the adjusting are performed without user-intervention.

* * * * *